(12) United States Patent
Komatsubara et al.

(10) Patent No.: US 9,265,234 B2
(45) Date of Patent: Feb. 23, 2016

(54) ABSORBENT ARTICLE FOR PET

(75) Inventors: Daisuke Komatsubara, Kagawa (JP); Takeshi Ikegami, Kagawa (JP)

(73) Assignee: Unicharm Corporation, Ehime (JP)

( * ) Notice: Subject to any disclaimer, the term of this patent is extended or adjusted under 35 U.S.C. 154(b) by 0 days.

(21) Appl. No.: 14/007,894

(22) PCT Filed: Mar. 13, 2012

(86) PCT No.: PCT/JP2012/056471
§ 371 (c)(1),
(2), (4) Date: Nov. 27, 2013

(87) PCT Pub. No.: WO2012/132889
PCT Pub. Date: Oct. 4, 2012

(65) Prior Publication Data
US 2014/0109843 A1    Apr. 24, 2014

(30) Foreign Application Priority Data

Mar. 30, 2011  (JP) .................... 2011-075847

(51) Int. Cl.
*A01K 23/00* (2006.01)
*A61F 13/15* (2006.01)

(52) U.S. Cl.
CPC ....... *A01K 23/00* (2013.01); *A61F 2013/15186* (2013.01)

(58) Field of Classification Search
CPC ................... A01K 23/00; A61F 2013/15186
USPC .................................. 119/869, 868, 867, 171
See application file for complete search history.

(56) References Cited

U.S. PATENT DOCUMENTS

| | | | | |
|---|---|---|---|---|
| 3,738,330 A | * | 6/1973 | Alofsin ................. | 119/838 |
| 4,209,016 A | * | 6/1980 | Schaar ................ | 604/390 |
| 4,996,949 A | * | 3/1991 | Wunderman et al. ..... | 604/390 |
| 5,137,508 A | * | 8/1992 | Engman ................ | 602/79 |
| 5,275,588 A | * | 1/1994 | Matsumoto et al. ...... | 604/372 |
| D383,259 S | * | 9/1997 | Post ................. | A01K 23/00 D24/124 |

(Continued)

FOREIGN PATENT DOCUMENTS

| | | |
|---|---|---|
| EP | 1 709 870 A1 | 10/2006 |
| JP | 2004-159592 A | 6/2004 |

(Continued)

OTHER PUBLICATIONS

International Search Report based on corresponding PCT application No. PCT/JP2012/056471 dated May 15, 2012 (4 pgs).

(Continued)

*Primary Examiner* — Rob Swiatek
*Assistant Examiner* — Ebony Evans
(74) *Attorney, Agent, or Firm* — Brinks Gilson & Lione

(57) ABSTRACT

An absorbent article for pet includes: a liquid permeable top surface layer, a liquid impermeable back surface layer, and an absorbent core disposed between the top surface layer and the back surface layer; the absorbent article for pet being configured to be in a belt-like shape and to be fit wrapped around a waist of a pet, in which the absorbent core includes: a belt-like absorbent core main body that extends from the first end portion side to the second end portion side in the longitudinal direction LD of the absorbent article for pet; and a first extension portion that extends outwards in a width direction from a first side edge in a central portion in the longitudinal direction of the absorbent core main body.

7 Claims, 15 Drawing Sheets

(56) References Cited

U.S. PATENT DOCUMENTS

| | | | |
|---|---|---|---|
| 6,371,950 B1* | 4/2002 | Roslansky | A61F 13/471 604/385.01 |
| 6,463,594 B2* | 10/2002 | Phillips | A41D 13/05 2/24 |
| 6,545,193 B1* | 4/2003 | Morgenstern | A61F 13/0273 128/876 |
| 6,710,221 B1* | 3/2004 | Pierce et al. | 604/361 |
| D566,909 S* | 4/2008 | Craig | D30/145 |
| D624,249 S* | 9/2010 | Ramos et al. | D30/145 |
| 8,020,523 B2 | 9/2011 | Ikegami et al. | |
| D693,524 S* | 11/2013 | Jangula | D30/145 |
| 2003/0040731 A1* | 2/2003 | Nozaki | A61F 13/47245 604/385.28 |
| 2006/0217678 A1 | 9/2006 | Ikegami et al. | |
| 2007/0129702 A1* | 6/2007 | Gribben | 604/392 |
| 2010/0319633 A1* | 12/2010 | Moncheski | A01K 23/00 119/869 |
| 2011/0209675 A1* | 9/2011 | Esperon | 119/868 |
| 2014/0165926 A1* | 6/2014 | Marks | 119/838 |

FOREIGN PATENT DOCUMENTS

| | | |
|---|---|---|
| JP | 2004-222868 A | 8/2004 |
| JP | 2006-271212 A | 10/2006 |
| JP | 2007-20533 A | 2/2007 |
| JP | 3141580 | 4/2008 |
| JP | 2010-207457 A | 9/2010 |
| WO | WO 01/95845 A1 | 12/2001 |

OTHER PUBLICATIONS

European extended Search Report based on corresponding European application No. 12764038.1 dated Feb. 24, 2015 (7 pgs).

Japanese Notice of Reasons for Rejection and English translation from corresponding Japanese application No. 2011-075847 dated Aug. 20, 2015 (4 pgs).

* cited by examiner

ABSORBENT ARTICLE FOR PET

RELATED APPLICATION

This application is a 35 U.S.C §371 national phase filing of International Patent Application No. PCT/JP2012/056471 filed Mar. 13, 2012, to which priority is claimed under 35 U.S.C. §120 and through which priority is claimed under 35 U.S.C. §119 Japanese Patent Application No. 2011-075847, filed Mar. 30, 2011.

TECHNICAL FIELD

The present invention relates to an absorbent article for pet, which is used wrapped around the waist of a pet such as a dog and a cat.

BACKGROUND ART

Heretofore, a disposable diaper for pet used for a pet such as a dog and a cat has been proposed. Such a disposable diaper for pet catches the feces and urine of the pet by covering the anus and the urethral opening positioned between the bases of the hind legs when being fit.

Some types of pets (for example miniature dachshunds which are dogs having long torsos and short legs) may have the urethral opening further forward than a position between the bases of the hind legs. In addition, male dogs have the urethral opening further forward than female dogs. If the disposable diaper for pet is fit on pets having the urethral opening further forward than a position between the bases of the hind legs, the urethral opening may not be covered by the diaper and urine may leak.

Given this, an absorbent article for pet that is used in a state of being wrapped around a pet's waist is proposed, the absorbent article for pet including an absorbent core in a rectangular belt shape, a liquid permeable top sheet disposed on a first face of the absorbent core, and a liquid impermeable back surface sheet disposed on a second face of the absorbent core, and being configured in a rectangular shape (see for example Patent Document 1).

Such an absorbent article for pet configured in a rectangular shape can be fit to cover the urethral opening infallibly, regardless of the position thereof.

Patent Document 1: Japanese Unexamined Patent Application Publication No. 2007-20533

DISCLOSURE OF THE INVENTION

Problems to be Solved by the Invention

When putting the absorbent article for pet on a pet, it is preferable to dispose the absorbent core such that the urinary organ of the pet is entirely covered therewith, in order to effectively absorb urine excreted by the pet. However, in a male pet, the base of a sex organ, which is the urinary organ, is located between the bases of the hind legs and the urethral opening is located at the tip side (front side of the body) of the sex organ. Given this, if a belt-like absorbent article for pet with a rectangular absorbent core is put on a male pet so as to cover the sex organ entirely, the absorbent core that is high in stiffness interferes with the hind legs of the pet. As a result, when such an absorbent article for pet was put on the pet, the absorbent core could not appropriately cover the base of the urinary organ (sex organ).

Therefore, the present invention is aimed at providing an absorbent article for pet that is fit in a state of being wrapped around the pet's waist, in which an absorbent core can appropriately cover the entire urinary organ.

Means for Solving the Problems

The present invention relates to an absorbent article for pet including: a liquid permeable top surface layer, a liquid impermeable back surface layer, and an absorbent core disposed between the top surface layer and the back surface layer; the absorbent article for pet being configured in a rectangular shape having a first end portion and a second end portion opposite each other, and a pair of side portions opposite each other orthogonal to the pair of the end portions, the absorbent article for pet being configured to be worn in a state of being wrapped around a waist of a pet, in which the absorbent core includes: a belt-like absorbent core main body that extends from a first end portion side to a second end portion side; and a first extension portion that extends outwards in a width direction from a first side edge in a central portion in a longitudinal direction of the absorbent core main body.

In addition, the absorbent article for pet preferably further includes: a pair of side sheets, disposed on respective top surface layer sides of the pair of side portions, with an outer edge joined with the top surface layer or the back surface layer and with at least a part of an inner edge being a free end; an elastic member attached to a vicinity of an inner edge of the pair of side sheets; and a pair of pocket portions formed between an inner face of the pair of side sheets and an outer face of the top surface layer, wherein a length of the pocket portion in a longitudinal direction of the absorbent article for pet is greater than a length of the first extension portion in the longitudinal direction of the absorbent article for pet.

In addition, the absorbent core preferably further includes a second extension portion that extends outwards in the width direction from a second side edge in the central portion in the longitudinal direction of the absorbent core main body.

In addition, an inner edge of the side sheet, among the pair of side sheets, disposed on a side where the first extension portion is provided, is preferably a free end spanning an overall length in the longitudinal direction.

The absorbent article for pet preferably further includes a position mark that indicates a position used as an index during putting on the absorbent article for pet.

The position mark is preferably disposed at a position corresponding to: the absorbent article main body; the first extension portion; or the second extension portion.

The position mark is disposed at a position that is visually recognizable from an outer face side of the back surface layer.

In addition, the position mark preferably changes in color when the absorbent core at the position where the position mark is disposed absorbs moisture.

Effects of the Invention

In the absorbent article for pet according to the present invention, when worn, the absorbent core can appropriately cover the entire urinary organ of a pet.

EXPLANATION OF REFERENCE NUMERALS

Figure 1:
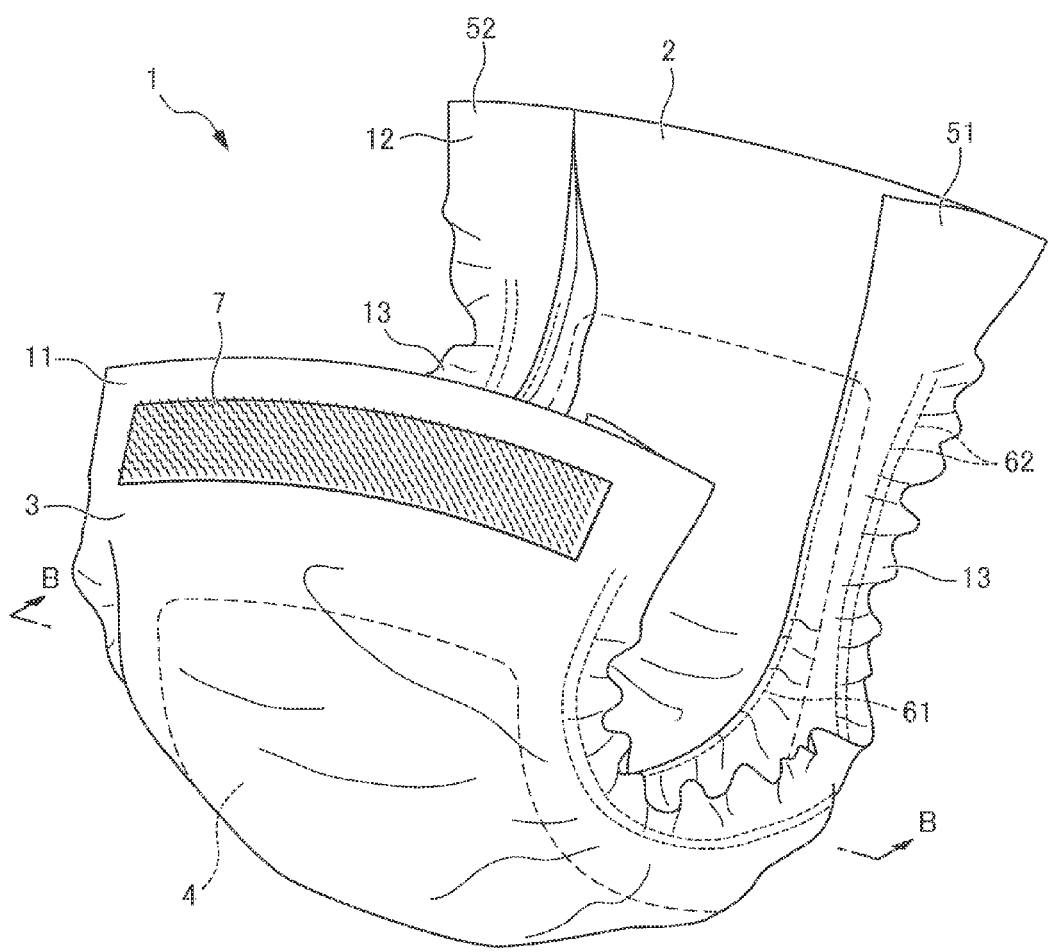
FIG. 1 is a perspective view showing an absorbent article for pet according to a first embodiment of the present invention.

1 Absorbent article for pet
2 Top sheet (Top layer)
3 Back surface layer
4 Absorbent core
8 Position mark
14 First pocket portion (Pocket portion)
15 Second pocket portion (Pocket portion)
41 Absorbent core main body
42 First extension portion
43 Second extension portion
51 First side sheet (Side sheet)
52 Second side sheet (Side sheet)
61 First elastic member (Elastic member)

Preferred Mode For Carrying Out The Invention

Preferred embodiments of the absorbent article for pet according to the present invention will be described hereinafter with reference to the drawings.

First, the absorbent article for pet according to the first embodiment will be described hereinafter with reference to FIGS. 1 to 6.

Figure 2:
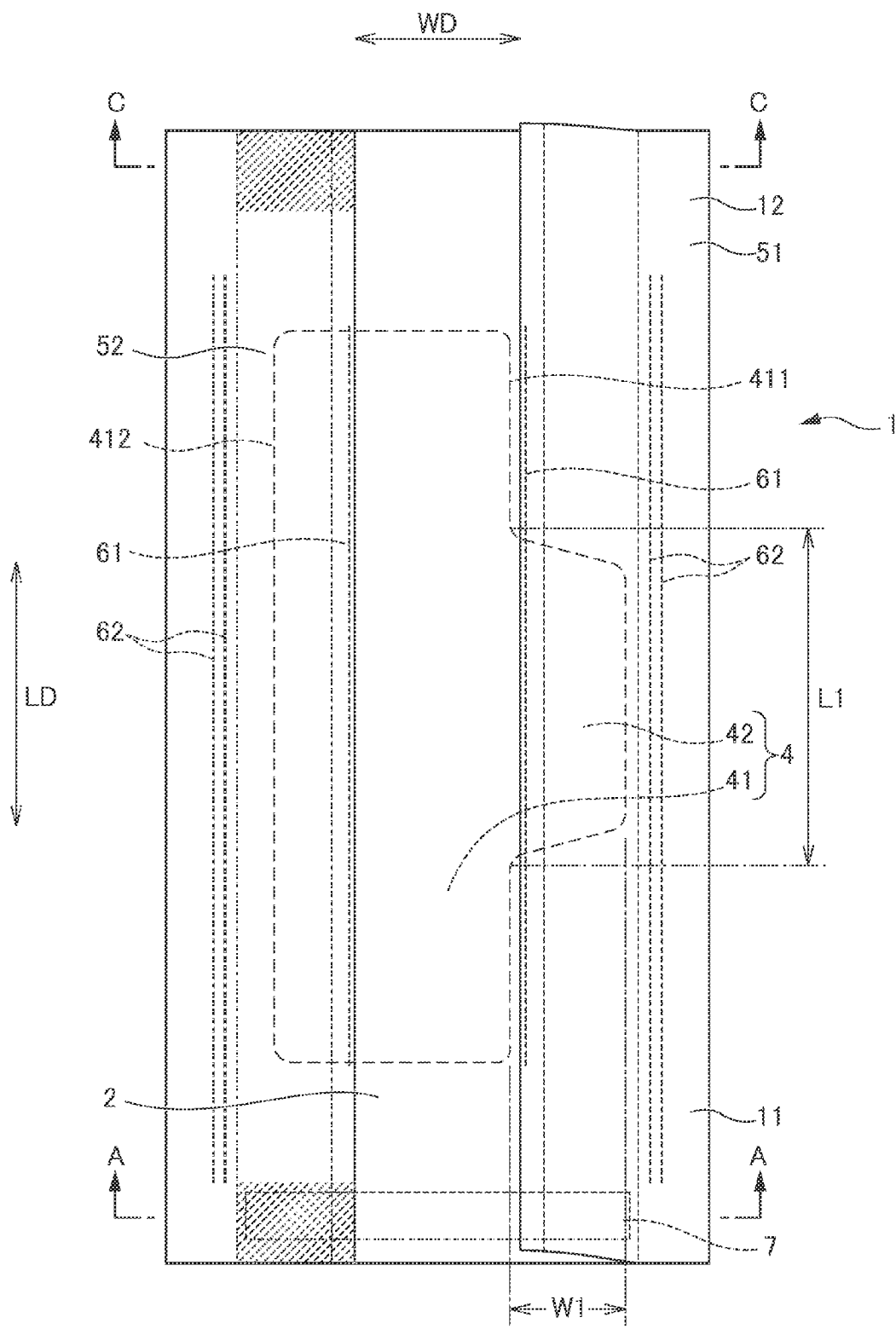
FIG. 2 is a plan view of the absorbent article for pet according to the first embodiment viewed from a top surface layer side.

As shown in FIGS. 1 and 2, an absorbent article for pet 1 according to the first embodiment is configured in a rectangular shape having a first end portion 11 and a second end portion 12 as a pair of end portions opposite each other and a pair of side portions opposite each other orthogonal to the first end portion 11 and the second end portion 12, the absorbent article for pet 1 being fit wrapped around the waist of a pet. The absorbent article for pet 1 is especially preferably used for a pet having the urethral opening located further toward the front than a position between the bases of the hind legs (for example, dogs with a long torso and short legs such as a miniature dachshund).

The absorbent article for pet 1 includes, as shown in FIGS. 1 to 6: a top sheet 2 constituting the liquid permeable top surface layer; a back surface sheet 31 and a waterproof sheet 32 constituting the liquid impermeable back surface layer 3; an absorbent core 4; a pair of side sheets 51, 52; a first elastic member 61 as the elastic member and a second elastic member 62; a hook tape 7; and the position mark 8.

The top sheet 2 is configured in a rectangular shape. The top sheet 2 mainly constitutes a surface of a side in contact with the body of the pet fitted with the article. As the top sheet 2, a perforated or non-perforated nonwoven fabric and a porous plastic sheet can be used. In the first embodiment, the top sheet 2 is preferably constituted of a nonwoven fabric from a viewpoint of appropriately engaging with the hook tape 7 (described later).

Figure 4:
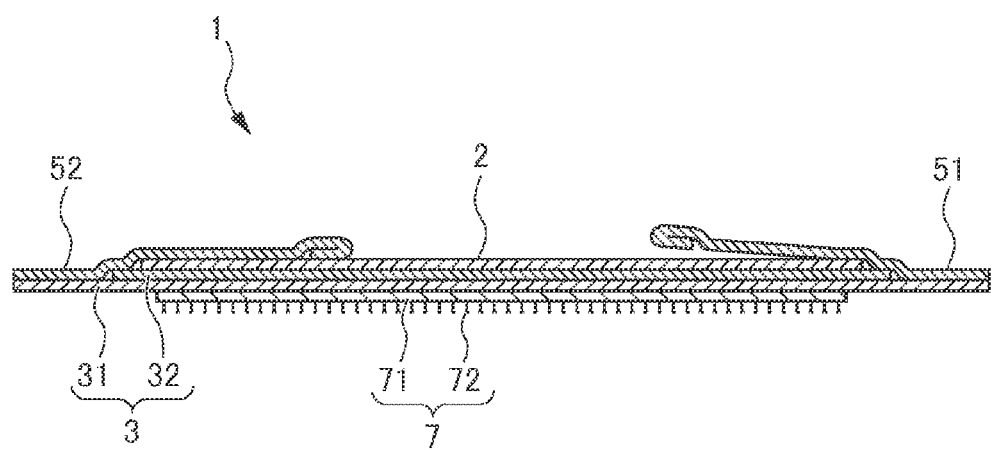
FIG. 4 is a cross-sectional view taken along the line A-A of FIG. 2.
Figure 5:
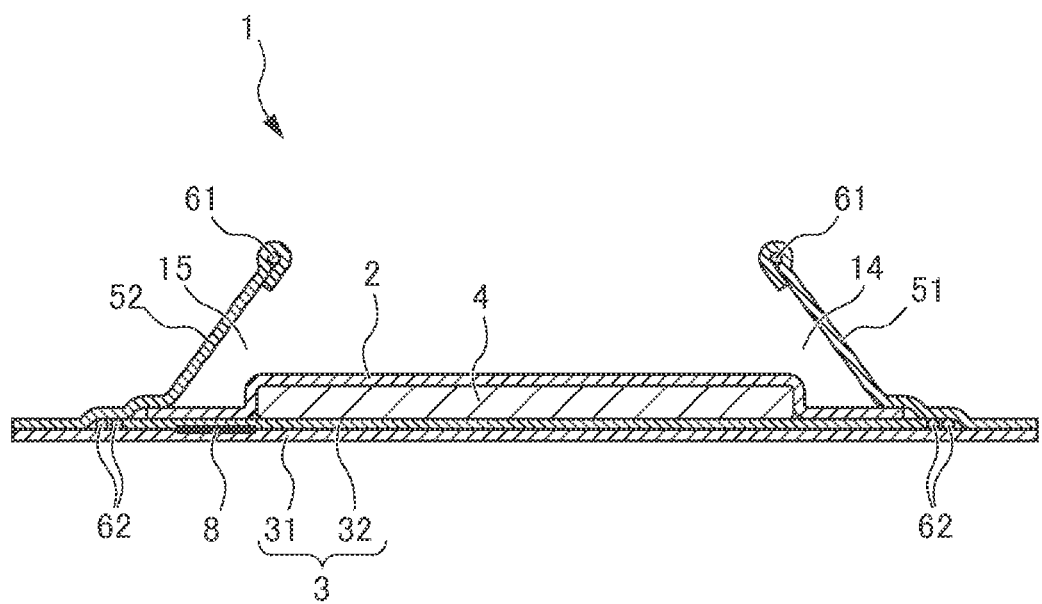
FIG. 5 is a cross-sectional view taken along the line B-B of FIG. 1.
Figure 6:
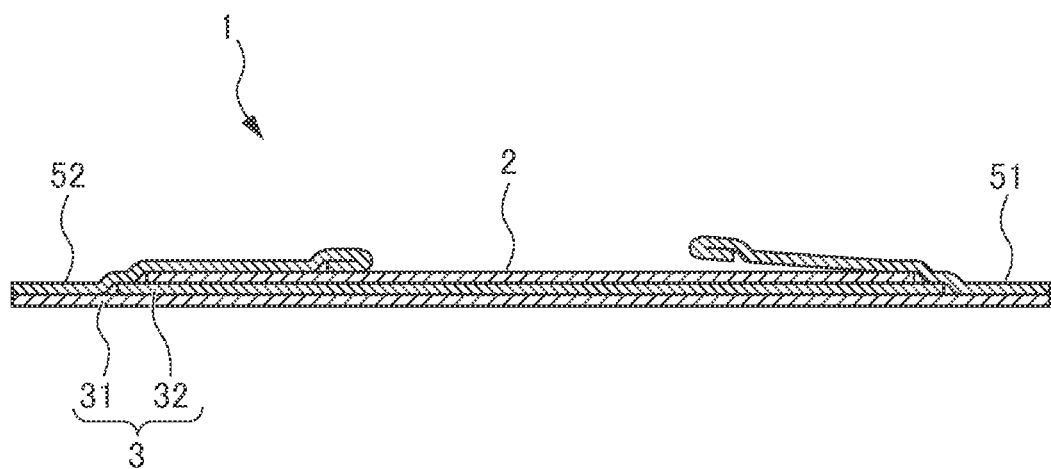
FIG. 6 is a cross-sectional view taken along the line C-C of FIG. 2.

The back surface sheet 31 is configured in a rectangular shape that is greater in width than the top sheet 2, and has substantially the same length as the top sheet 2, as shown in FIGS. 4 to 6. The back surface sheet 31 constitutes a surface of the absorbent article for pet 1, on a side not in contact with the pet's body.

The waterproof sheet 32 is configured to be smaller in width than the back surface sheet 31 and greater in width than the top sheet 2 and disposed on a surface of a top sheet 2 side of the back surface sheet 31.

As the back surface sheet 31 and the waterproof sheet 32, a hydrophobic nonwoven fabric, a liquid impermeable plastic film, a laminated sheet made of the nonwoven fabric and the liquid impermeable plastic film, an SMS nonwoven fabric made by sandwiching a high-water resistance melt-blown nonwoven fabric with a high-strength spun-bond nonwoven fabric, and the like can be used.

The pair of side sheets 51, 52 are configured in an elongated rectangular shape as shown in FIG. 2 and disposed on respective side portions along the longitudinal direction of a body side of the top sheet 2. The pair of side sheets 51, 52 are configured to have substantially the same length as the top sheet 2 and the back surface sheet 31. As shown in FIGS. 4 to 6, outer edges of the pair of side sheets 51, 52 correspond to side edges of the back surface sheet 31. The outer edges of the pair of side sheets 51, 52 are joined with the side edges of the back surface sheet 31.

A part of the inner edges of the pair of side sheets 51, 52 is a free-end, as shown in FIGS. 1 and 5. More specifically, the pair of side sheets 51, 52 is constituted of a first side sheet 51 that is placed on a front side of the pet's body and a second side sheet 52 that is placed on a back side of the pet's body upon putting the absorbent article for pet 1 on the pet.

As shown in FIGS. 4 to 6, the inner edge of the first side sheet 51 is a free end in an overall length in the longitudinal direction LD of the absorbent article for pet 1.

The inner edge of the second side sheet 52 is joined to the top sheet 2 in the first end portion 11 and the second end portion 12, as shown in FIGS. 4 and 6. In addition, the inner edge of the second side sheet 52 is a free end, except for the first end portion 11 and the second end portion 12, as shown in FIG. 5.

As the side sheets 51, 52, a water repellent or hydrophobic sheet is preferably used. More specifically, various nonwoven fabrics such as spun lace nonwoven fabric, spun bond nonwoven fabric, thermal bond nonwoven fabric, melt-blown nonwoven fabric, needle-punched nonwoven fabric, air-through nonwoven fabric and the like can be used. As the fiber constituting the nonwoven fabric, synthetic fiber of olefin, polyester, polyamide and the like such as polyethylene and polypropylene; regenerated fiber such as rayon and cupra; and natural fiber such as cotton can be used.

Figure 3:
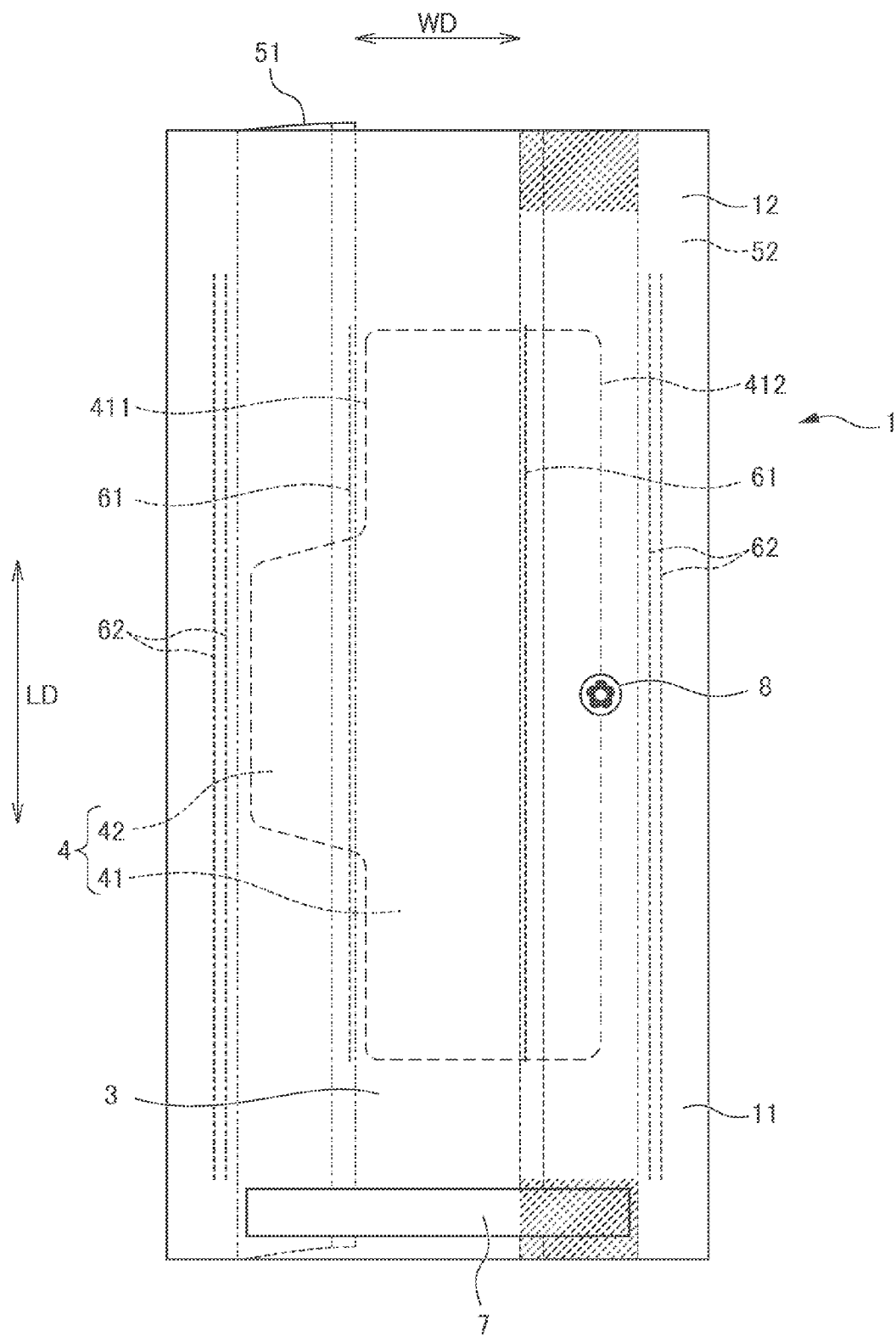
FIG. 3 is a plan view of the absorbent article for pet according to the first embodiment viewed from a back surface layer side.

The absorbent core 4 is disposed between the top sheet 2 and the back surface layer 3 that are layered, as shown in FIG. 4. The absorbent core 4 includes a rectangular belt shaped absorbent core main body 41 and a first extension portion 42 that extends from the absorbent core main body 41, as shown in FIGS. 2 and 3.

The absorbent core main body 41 is disposed to extend from one end side to the other end side of the absorbent article for pet 1 in the longitudinal direction LD.

The absorbent core main body 41 is configured to be smaller in length than the top sheet 2 and the back surface sheet 3. The absorbent core main body 41 is not disposed in the first end portion 11 which is one end and the second end portion 12 which is the other end in the longitudinal direction LD of the absorbent article for pet 1.

Width of the absorbent core main body 41 is configured to be smaller than width of the top sheet 2 and the back surface sheet. The absorbent core main body 41, as shown in FIG. 2, is disposed offset toward a side on which the second side sheet 52 is disposed in the width direction WD of the absorbent article for pet 1. More specifically, as shown in FIG. 2, a first side portion 411, which is one side portion of the pair of side portions along the longitudinal direction of the absorbent core main body 41, is located in the vicinity of the position of the first elastic member 61 disposed on the first side sheet 51 in a planar view. On the other hand, a second side portion 412, which is another side portion of the pair of side portions along the longitudinal direction of the absorbent core main body 41, is located more outward in the width direction WD of the absorbent article for pet 1, than the first elastic member 61 disposed on the second side sheet 52.

The first extension portion 42 extends outward in the width direction from a central portion in the longitudinal direction of the absorbent core main body 41. More specifically, the first extension portion 42 is disposed on the first side portion 411 side among the pair of side portions along the longitudinal direction of the absorbent core main body 41. A length L1 of the first extension portion 42 in the longitudinal direction LD of the absorbent article for pet 1 is preferably 150 mm to 600 mm, or 30% to 90% of the length of the absorbent article for pet 1, from a viewpoint of appropriately covering a lower face of the urinary organ of the pet. A length W1 of the first extension portion 42 in the width direction WD of the absorbent article for pet 1 is preferably 10 mm to 100 mm, or 10% to 50% of the width of the absorbent core 4, from a viewpoint of appropriately covering a base of the urinary organ of the pet.

Figure 13:
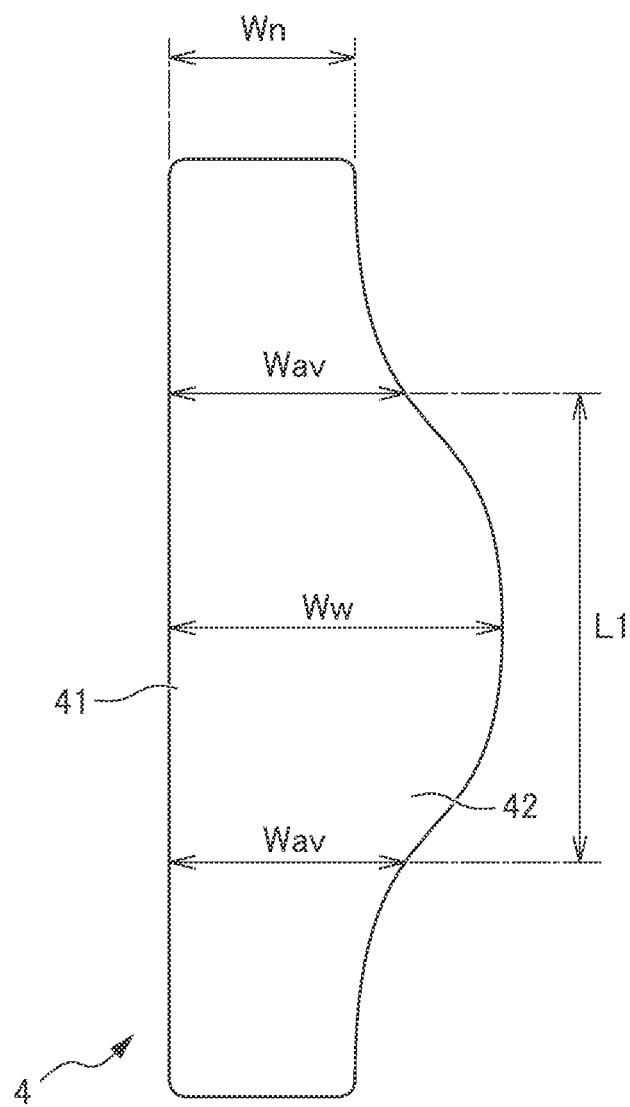
FIG. 13 is a diagram illustrating an example of a shape of the absorbent core.

In a case in which the first extension portion 42 is in a shape smoothly projecting from the absorbent article main body 41 as shown in FIG. 13, the length L1 of the first extension portion 42 in the longitudinal direction LD of the absorbent article for pet 1 is calculated as follows.

Wn is a width of the narrowest part of the absorbent core 4; Ww is a width of the widest part of the absorbent core 4; Wav is a deemed width of the extension portion obtained by averaging the width Wn and Ww (Wn+Ww/2). And then, a length between two positions having the deemed width of the extension portion Wav in the absorbent core 4 is considered to be the length L1 of the first extension portion 42 in the longitudinal direction LD of the absorbent article for pet 1.

As the absorbent core 4, fluff pulp and high absorbance polymer wrapped with a core wrapping material such as tissue can be used.

As the fluff pulp used in the absorbent core 4, chemical pulp, cellulose fiber, and artificial cellulose fiber such as rayon, acetate, and the like can be exemplified. As the high absorbance polymer, granulous or fibrous polymer of starch, acrylic acid, and amino acid can be exemplified.

The first elastic member 61 is disposed in the vicinity of the inner edge of the first side sheet 51 and the second side sheet 52, as shown in FIGS. 1 and 2. More specifically, the first elastic member 61 is sandwiched by the side sheet that is folded back from the inner edge side and fixed to the side sheet by a hotmelt adhesive in an extended state as shown in FIG. 5. The first elastic member 61 is, in the extended state, substantially the same in length as the absorbent core (absorbent core main body 41) in the longitudinal direction and is disposed on the first side sheet 51 and the second side sheets 52 as shown in FIG. 2.

The second elastic member 62 is disposed on each of the pair of side portions along the longitudinal direction LD of the absorbent article for pet 1, as shown in FIGS. 1 and 2. More specifically, the second elastic member 62 is disposed between the first side sheet 51 and the second side sheet 31, and between the second side sheet 52 and the back surface sheet 31, as shown in FIG. 5. In addition, the second elastic member 62 is fixed to the side sheets 51, 52 and the back surface sheet 31 by a hotmelt adhesive.

The second elastic member 62 is, in the extended state, greater in length than the absorbent core 4 in the longitudinal direction and is disposed on each of the pair of side portions along the longitudinal direction LD of the absorbent article for pet 1.

As the first elastic member 61 and the second elastic member 62, any material that is elongated and stretchable can be used, for example: natural rubber such as filiform rubber and flat rubber; thermoplastic elastomer such as urethane, ethylene-vinyl acetate copolymer (EVA), and PE. More specifically, as the thermoplastic elastomer, polybutadiene, polyisoprene, styrene-butadiene copolymer, styrene-isoprene copolymer, polyurethane, ethylene-vinyl acetate copolymer, ethylene-α-olefin copolymer and the like that are processed to be filiform or formed in a film and then slitted into thin strips can be exemplified.

The hook tape 7 is disposed on an outer face of the first end portion 11 of the absorbent article for pet 1, as shown in FIGS. 1 to 3. The hook tape 7 is configured in a belt like shape and disposed such that the longitudinal direction thereof is along the width direction WD of the absorbent article for pet 1. In addition, the hook tape 7 is preferably attached at a position away from the side edge of the first end portion 11 by a predetermined distance.

As shown in FIG. 4, the hook tape 7 includes a belt-shaped base portion 71 and a plurality of hook portions 72 provided on one face of the base portion 71. The hook tape 7 is attached to the back surface sheet 31 such that the face on which the plurality of hook portions 72 are formed is directed outward.

The position mark 8 indicates a position used as an index when fitting the absorbent article for pet 1 to the pet. In the first embodiment, the position mark 8 is disposed on an outer side of the back surface layer 3, as shown in FIG. 3. The position mark 8 is disposed on a side on which the second side sheet 52 is disposed in the width direction WD, in a central portion in the longitudinal direction LD of the absorbent article for pet 1. In the first embodiment, the position mark 8 indicates a part that should be positioned on a front side of the pet's body when fitting the absorbent article for pet 1 to the pet.

In the first embodiment, the position mark 8 is constituted of a sticker member with a flower pattern and disposed between the waterproof sheet 32 and the back surface sheet 31 (see FIG. 5). The position mark 8 is visible from an outer side of the back surface layer 3, through the back surface sheet 31.

With the position mark 8, it is easy to understand which side portion of the belt-shaped absorbent article for pet 1 should be positioned on the front side of the pet's body, even when the absorbent article for pet 1 is viewed from the back surface layer 3 side.

The position mark 8 can be constituted of a material that changes in color when the absorbent core 4 that is disposed at the position of the position mark 8 absorbs moisture. By checking the color of the position mark 8, time to replace the absorbent article for pet 1 can be recognized appropriately.

Alternatively, the position mark 8 can be configured by printing on the outer side of the back surface layer 3.

In the above-described absorbent article for pet 1, the first elastic member 61 in the extended state is fixed to the first side sheet 51 and the second side sheet 52 along the longitudinal direction LD of the absorbent article for pet 1. In addition, the second elastic member 62 in the extended state is fixed between the side sheets 51, 52 and the back surface sheet 31, along the longitudinal direction LD of the absorbent article for pet 1.

Given this, the absorbent article for pet 1 in a natural state (without external force applied) has a solid shape as shown in FIG. 1, with the first elastic member 61 and the second elastic member 62 being contracted to thereby bring the first end portion 11 and the second end portion 12 close to each other, with the top sheet 2 side constituting an inner face. A pair of waist gather portions 13 that are stretchable in the longitudinal direction LD are thus formed on a pair of side portions along the longitudinal direction LD of the absorbent article for pet 1 (see FIG. 1).

In addition, on the free end sides of the first side sheet 51 and the second side sheet 52, mainly parts where the first elastic member 61 is disposed lift, to thereby form a first pocket portion 14 between the inner face of the first side sheet 51 and the outer face of the top sheet 2, and a second pocket portion 15 between the inner face of the second side sheet 52 and the outer face of the top sheet 2 (see FIG. 4).

Here, the length of the first pocket portion 14 in the longitudinal direction LD of the absorbent article for pet is configured to be greater than a length L1 of a first extension portion 42 in the longitudinal direction LD of the absorbent article for pet. More specifically, the first pocket portion 14 is configured by making the inner edge of the first side sheet 51 a free end spanning the overall length in the longitudinal direction. As a result, the first pocket portion (the first side sheet 51) is configured to easily lie outward in the width direction WD of the absorbent article for pet 1, from a state in which the free end side thereof is upright.

On the other hand, the second pocket portion 15 is configured by joining one end portion and another end portion in the longitudinal direction of an inner edge of the second side sheet 52 with the top sheet 2, while making other parts except for the one end portion and another end portion a free end. As a result, the second pocket portion 15 (the second side sheet 52) is configured to be more difficult to lie outward in the width direction WD of the absorbent article for pet 1, compared to the first pocket portion 14.

Figure 7:
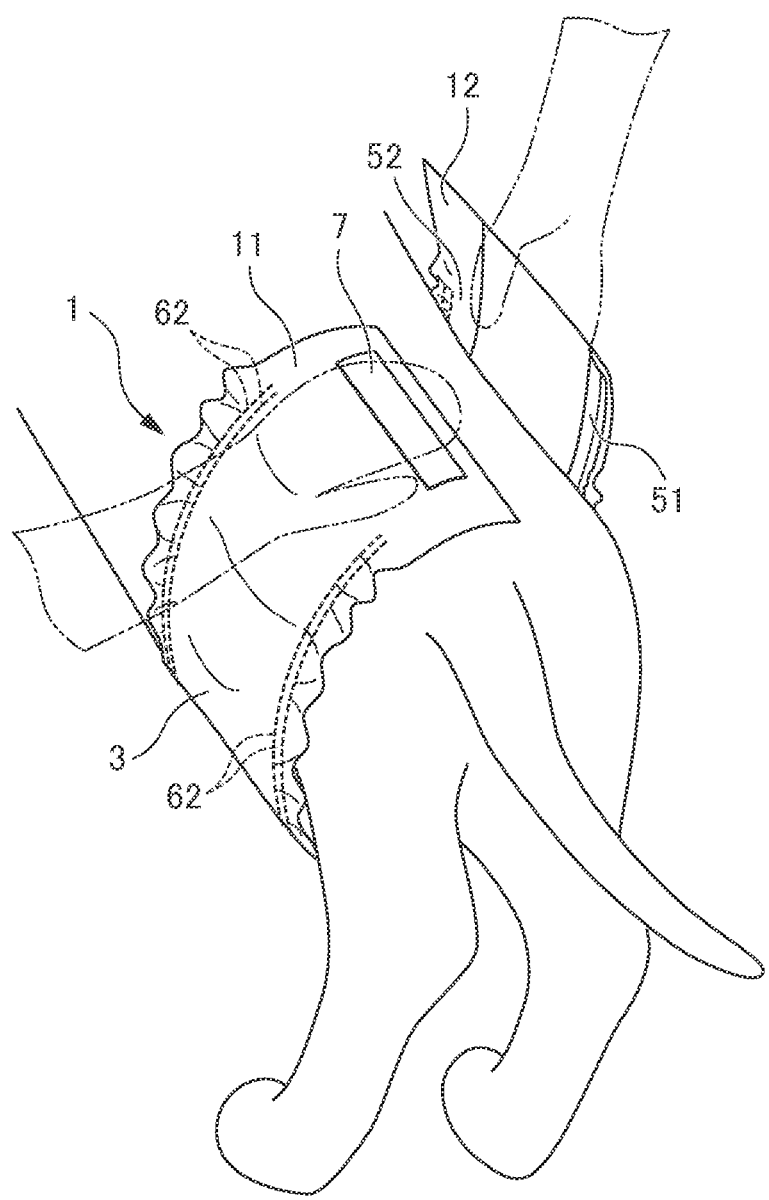
FIG. 7 is a diagram illustrating a process of putting the absorbent article for pet on a pet, in which the first end portion is placed on the pet's back.
Figure 8:
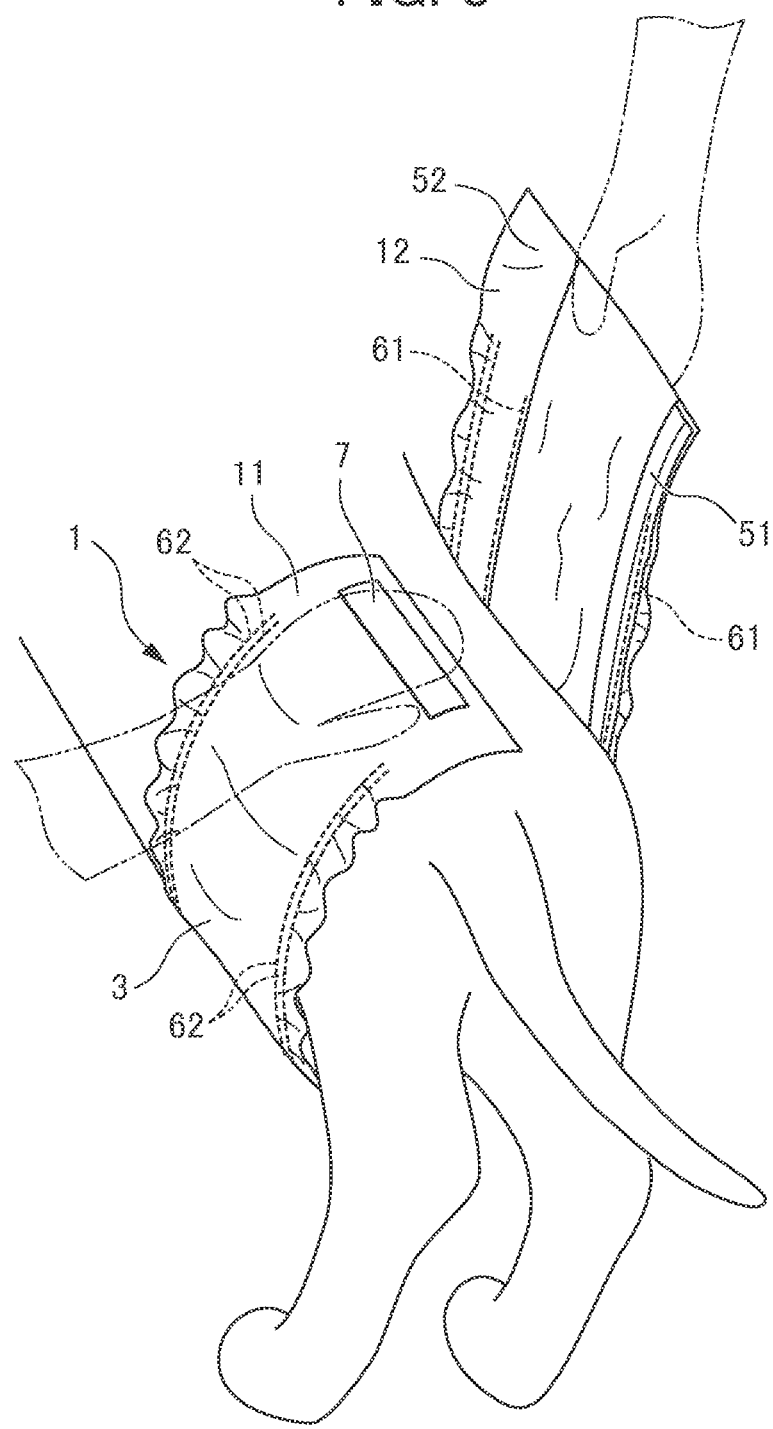
FIG. 8 is a diagram illustrating a process of putting the absorbent article for pet on a pet, in which the second end portion of the absorbent article for pet wrapped around the waist of the pet is pulled to bring the absorbent article for pet into close contact with the waist of the pet.
Figure 9:
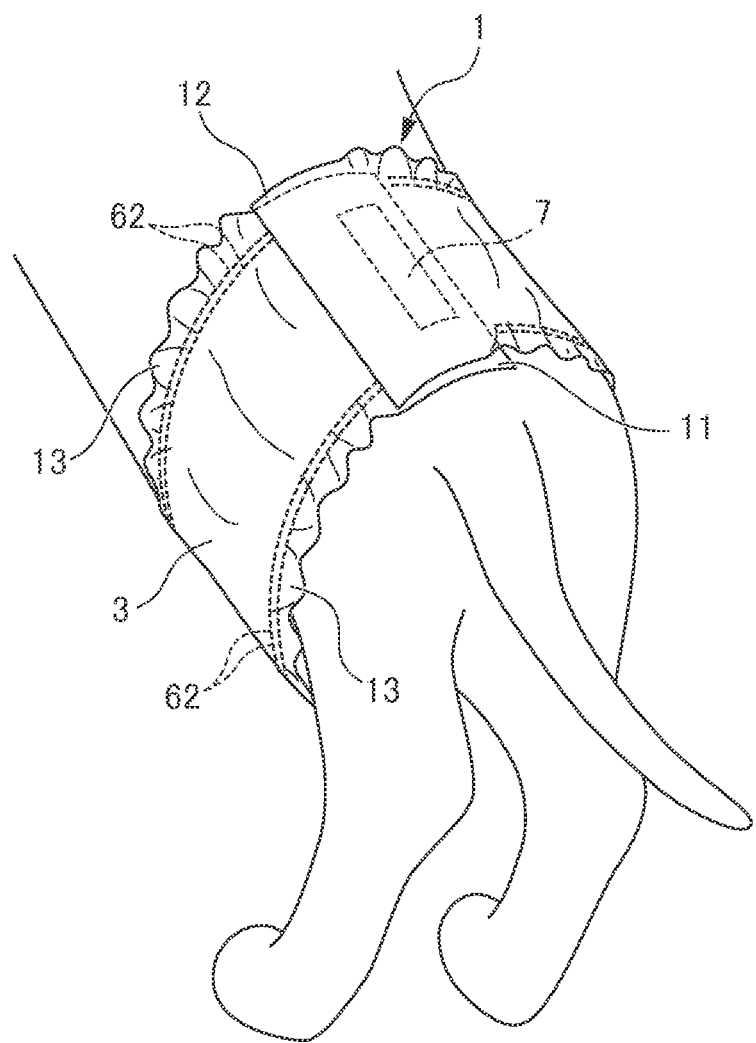
FIG. 9 is a diagram illustrating a state in which the absorbent article for pet is put around the pet's waist.
Figure 10:
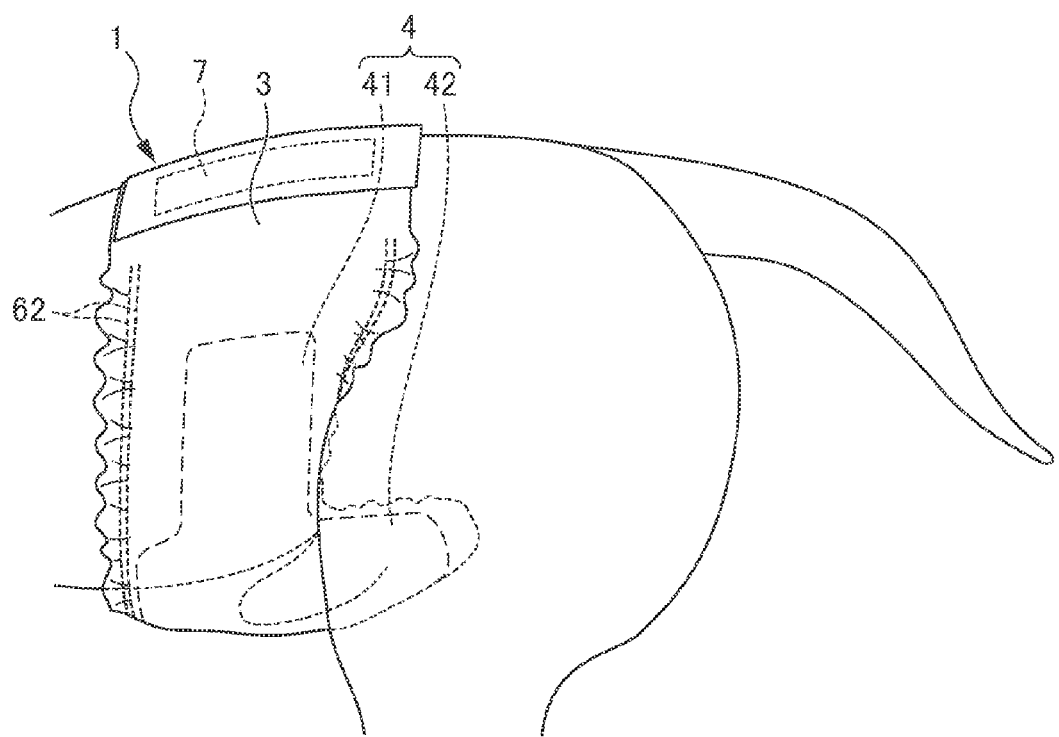
FIG. 10 is a diagram illustrating a state in which the absorbent article for pet is put around the pet's waist, viewed from a left side of the pet.

Next, steps of putting on the absorbent article for pet 1 according to the first embodiment to a pet will be described hereinafter with reference to FIGS. 7 to 10. FIGS. 7 to 10 are diagrams illustrating a process of fitting the absorbent article for pet 1 on a pet: FIG. 7 is a diagram illustrating a state in which the first end portion 11 is placed on the pet's back; FIG. 8 is a diagram illustrating a process of putting the absorbent article for pet 1 on a pet, in which the second end portion 12 of the absorbent article for pet 1 wrapped around the waist of the pet is pulled to bring the absorbent article for pet 1 into close contact with the waist of the pet; FIG. 9 is a diagram illustrating a state in which the absorbent article for pet 1 is fit around the pet's waist; and FIG. 10 is a diagram illustrating a state in which the absorbent article for pet 1 is fit around the pet's waist, viewed from a left side of the pet.

First, as shown in FIG. 7, the first end portion 11 of the absorbent article for pet 1 is placed on the back of the pet and the vicinity of the first end portion 11 is held by one hand of a person fitting the article. Here, a side on which the position mark 8 is provided is placed on the front side of the pet's body, based on the position mark 8 disposed on the back surface layer 3 side.

Thereafter, in a state in which the first end portion 11 is held by one hand, the second end portion 12 of the absorbent article for pet 1 is held by the other hand and wrapped around the pet's body to cover the abdomen of the pet.

Next, as shown in FIG. 8, the second end portion 12 is pulled upward and the pair of waist gather portions 13 is brought into close contact with the pet's waist; and then, as shown in FIG. 9, the inside of the second end portion 12 is engaged with the hook tape 7 provided on the outer face of the first end portion 11. The absorbent article for pet 1 is thus wrapped around the pet's waist.

In the abovementioned process, upon fitting on the absorbent article for pet 1 to the pet, the absorbent article for pet 1 is brought close to the hind leg side of the pet's body and wrapped around the pet's body, so as to cover the entire urinary organ of the pet by the absorbent core 4. In the first embodiment, the absorbent core main body 41 is disposed offset toward the side on which the second side sheet 52 is disposed (the front side of the pet's body) in the width direction WD of the absorbent article for pet 1. In addition, the first extension portion 42 extends outward in the width direction WD of the absorbent article for pet 1 (to the back side of the pet's body). The first extension portion 42 can thus be disposed to cover a lower portion of the base of the pet's urinary organ, positioned between the hind legs, as shown in FIG. 10. In addition, the absorbent core main body 41 is not provided in a part of the absorbent article for pet 1 disposed close to the pet's hind legs. In addition, since the absorbent core 4 (the absorbent core main body 41) does not interfere with the pet's hind legs when the absorbent article for pet 1 is wrapped around the pet's body, the absorbent article for pet 1 can be appropriately wrapped around the pet's body at a position close to the hind legs.

Furthermore, the first pocket portion 14 is configured to be easier to lie outward in the width direction WD of the absorbent article for pet 1. Therefore, when the absorbent article for pet 1 is wrapped around the pet's body, the first pocket portion 14 (the first side sheet 51) in a state of lying outward can be disposed to appropriately cover the lower part and back part of the base of the pet's urinary organ (see FIGS. 7 to 9).

The above-described absorbent article for pet 1 according to the first embodiment provides the following operation and effects.

(1) The absorbent core main body 41 is disposed offset toward the side on which the second side sheet 52 is disposed (the front side of the pet's body) in the width direction WD of the absorbent article for pet 1, and the first extension portion 42 is provided extending outward in the width direction WD of the absorbent article for pet 1. The first extension portion 42 can thus be disposed to cover a lower portion of the base of the pet's urinary organ, positioned between the hind legs. In addition, the absorbent core main body 41 is not provided in a part of the absorbent article for pet 1 disposed close to the pet's hind legs. In addition, since the absorbent core 4 (the absorbent core main body 41) does not interfere with the pet's hind legs when the absorbent article for pet 1 is wrapped around the pet's body, the absorbent article for pet 1 can be appropriately wrapped around the pet's body at a position close to the hind legs. In other words, in the absorbent article for pet that is fit wrapped around the pet's waist, the absorbent core 4 can appropriately cover the entire urinary organ.

(2) The absorbent core main body 41 is disposed to extend from a first end side to a second end side in the longitudinal direction LD of the absorbent article for pet 1. As a result, when the absorbent article for pet 1 is fit on the pet, the absorbent core main body 41 can be arranged also in side portions of the pet's body, except for a part between the hind legs in which the first extension portion 42 is provided. Therefore, even if the pet urinates while lying down, urine can be appropriately absorbed by the absorbent core main body 41 disposed on the side portions of the pet's body.

(3) The second side portion 412 of the absorbent core main body 41 is positioned more outward in the width direction WD than the first elastic member 61 disposed on the second side sheet 52. As a result, the absorbent core main body 41 can be disposed deep inside the second pocket portion 15 and the absorbent core 4 can cover broadly a position of the urethral opening in front of a position between the bases of the hind legs in the pet's body. Leakage prevention performance of the absorbent article for pet 1 can thus be further improved.

(4) The length of the first pocket portion 14 in the longitudinal direction LD is configured to be greater than a length of the first extension portion 42 in the longitudinal direction LD. The degree of freedom of movement of a free end side of the first pocket portion 14 can thus be improved. As a result, upon putting the absorbent article for pet 1 on a pet, the free end side of the first pocket portion 14 can be flexibly deformed so as to cover a lower portion of the base of the pet's urinary organ.

(5) The first pocket portion 14 is configured by making the inner edge of the first side sheet 51 a free end spanning the overall length in the longitudinal direction. As a result, the first pocket portion 14 can be made easier to lie outward in the width direction WD of the absorbent article for pet 1. Therefore, when the absorbent article for pet 1 is wrapped around the pet's body, the first pocket portion 14 (the first side sheet 51) in a state of lying outward can be disposed to appropriately cover the lower part and back part of the base of the pet's urinary organ. The absorbent article for pet 1 can thus be easily fit on the pet in an appropriate state.

(6) The position mark 8 indicating a part that should be positioned on the front side of the pet's body is provided at a position visible from the outside of the back surface layer 3. It is thus easy to understand which side portion of the belt-shaped absorbent article for pet 1 should be positioned on the front side of the pet's body, even when the absorbent article for pet 1 is viewed from the back surface layer 3 side.

Figure 11:
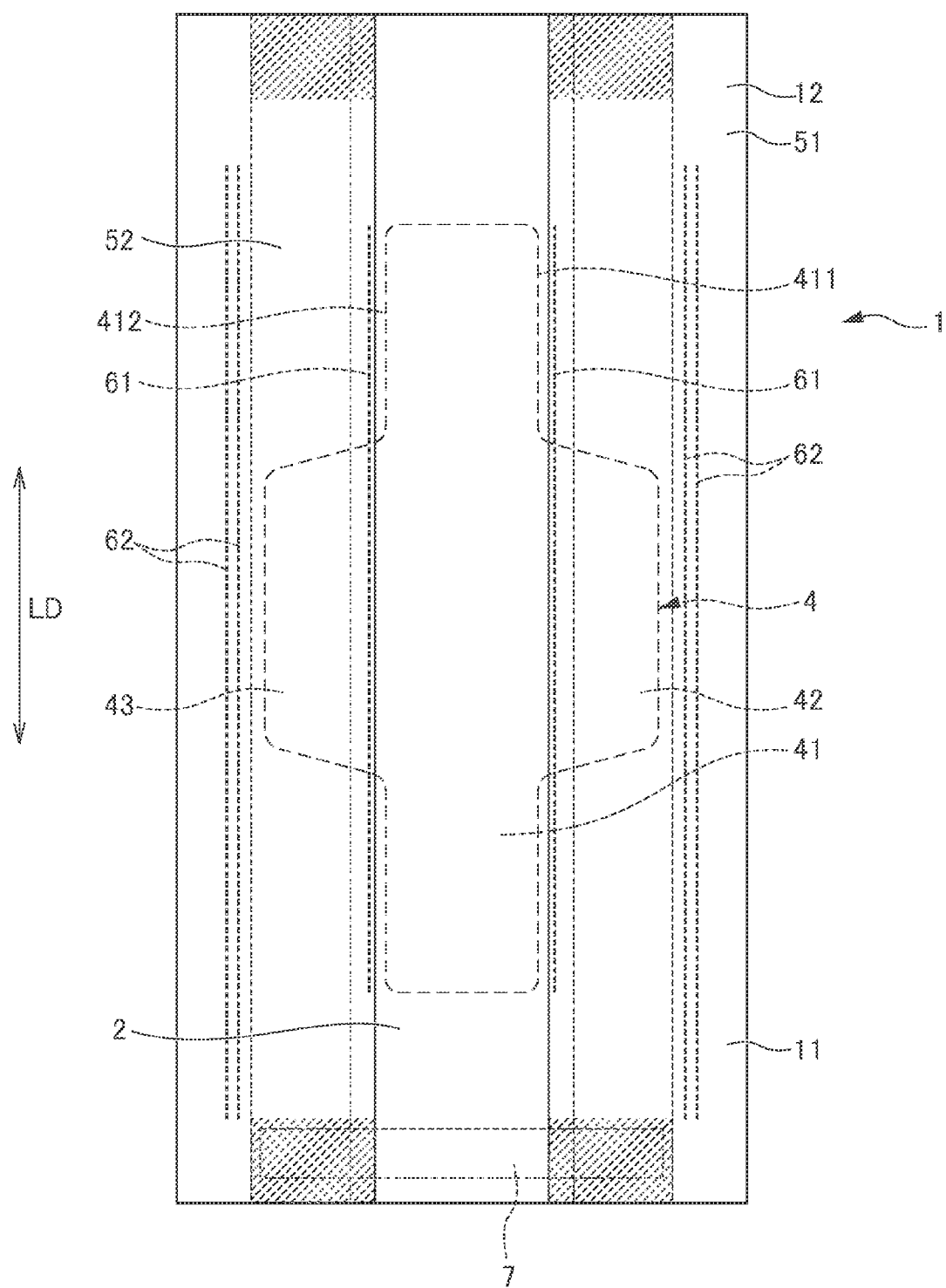
FIG. 11 is a plan view of the absorbent article for pet according to the second embodiment viewed from the top surface layer side.

The absorbent article for pet 1 according to the second embodiment will be described hereinafter with reference to FIG. 11. FIG. 11 is a plan view of the absorbent article for pet 1 according to the second embodiment.

In the description of the following embodiments, the same constituent features are referred by the same reference numerals and description thereof is omitted or simplified.

The absorbent article for pet 1 according to the second embodiment is different from the first embodiment mainly in the configuration of the absorbent core 4.

As shown in FIG. 11, the absorbent core 4 of the second embodiment further includes the second extension portion 43 that extends outward in the width direction from the second side portion 412 of the absorbent core main body 41. In the second embodiment, the width of the absorbent article main body 41 is configured to be smaller than in the first embodiment. More specifically, as shown in FIG. 11, the first side portion 411 of the absorbent core main body 41 is located in the vicinity of the location of the first elastic member 61 disposed on the first side sheet 51 in a planar view. The second side portion 412 of the absorbent core main body 41 is located in the vicinity of the location of the first elastic member 61 disposed on the second side sheet 52 in a planar view.

The second extension portion 43 is disposed on the second side portion 412 in a central portion in the longitudinal direction of the absorbent core main body 41.

The second extension portion 43 is configured in the same shape and same size as the first extension portion 42. In addition, in the second embodiment, the inner edge of the first side sheet 51 is joined with the top sheet 2 in the first end portion and the second end portion in the longitudinal direction LD, while a part between the first end portion and the second end portion is a free end.

The absorbent article for pet 1 according to the second embodiment provides the following effects, in addition to the above effects (1), (2), (4) and (6).

(7) The absorbent core 4 is configured to include the second extension portion 43 that extends outward in the width direction from the second side portion 412 of the absorbent core main body 41. The absorbent core 4 can thus be configured to have linear symmetry about a central line extending in the longitudinal direction LD of the absorbent article for pet 1. As a result, when fitting the absorbent article for pet 1 on the pet, the absorbent core 4 can appropriately cover the entire urinary organ of the pet regardless of the orientation of fitting the absorbent article for pet 1.

The preferred embodiments of the present invention have been described; however, the present invention is not limited thereto and can be modified accordingly.

For example, the position mark 8 is disposed on the back surface layer 3 side in the first embodiment; however, the present invention is not limited thereto. In other words, the position mark can also be disposed on the top sheet side.

Figure 12A:
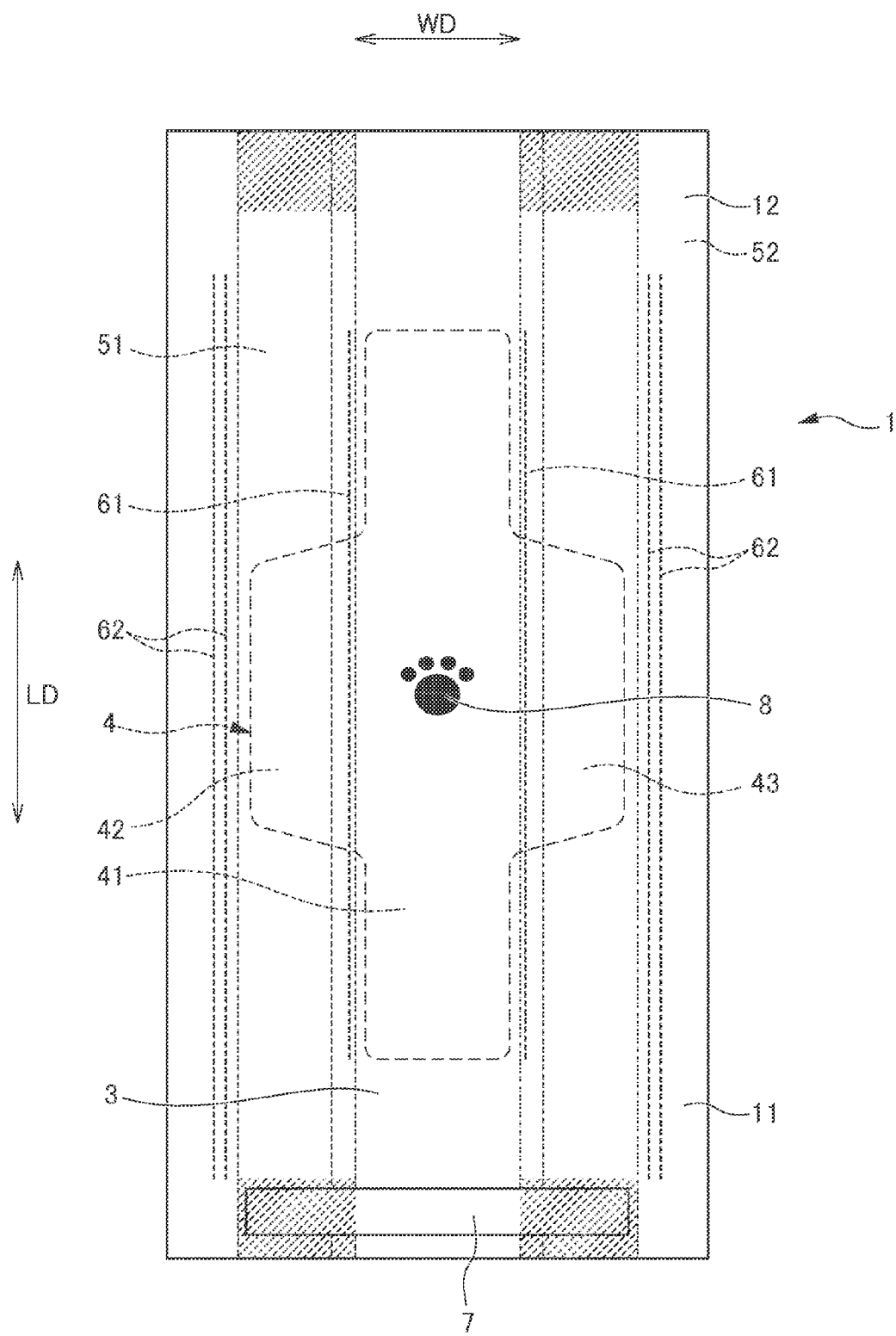
FIG. 12A is a diagram illustrating an example of arrangement of a position mark.

In addition, in the first embodiment, the position mark 8 is disposed on a side on which the second side sheet 52 is disposed in the width direction WD, in a central portion in the longitudinal direction LD of the absorbent article for pet 1; however, the present invention is not limited thereto. The position mark 8 can be disposed in the central portion of the absorbent core main body 41, as shown in FIG. 12A. Alternatively, the position mark 8 can be disposed on a side on which the second extension portion 43 is disposed, in the width direction WD of the absorbent article for pet 1, as shown in FIG. 12B.

Figure 12B:
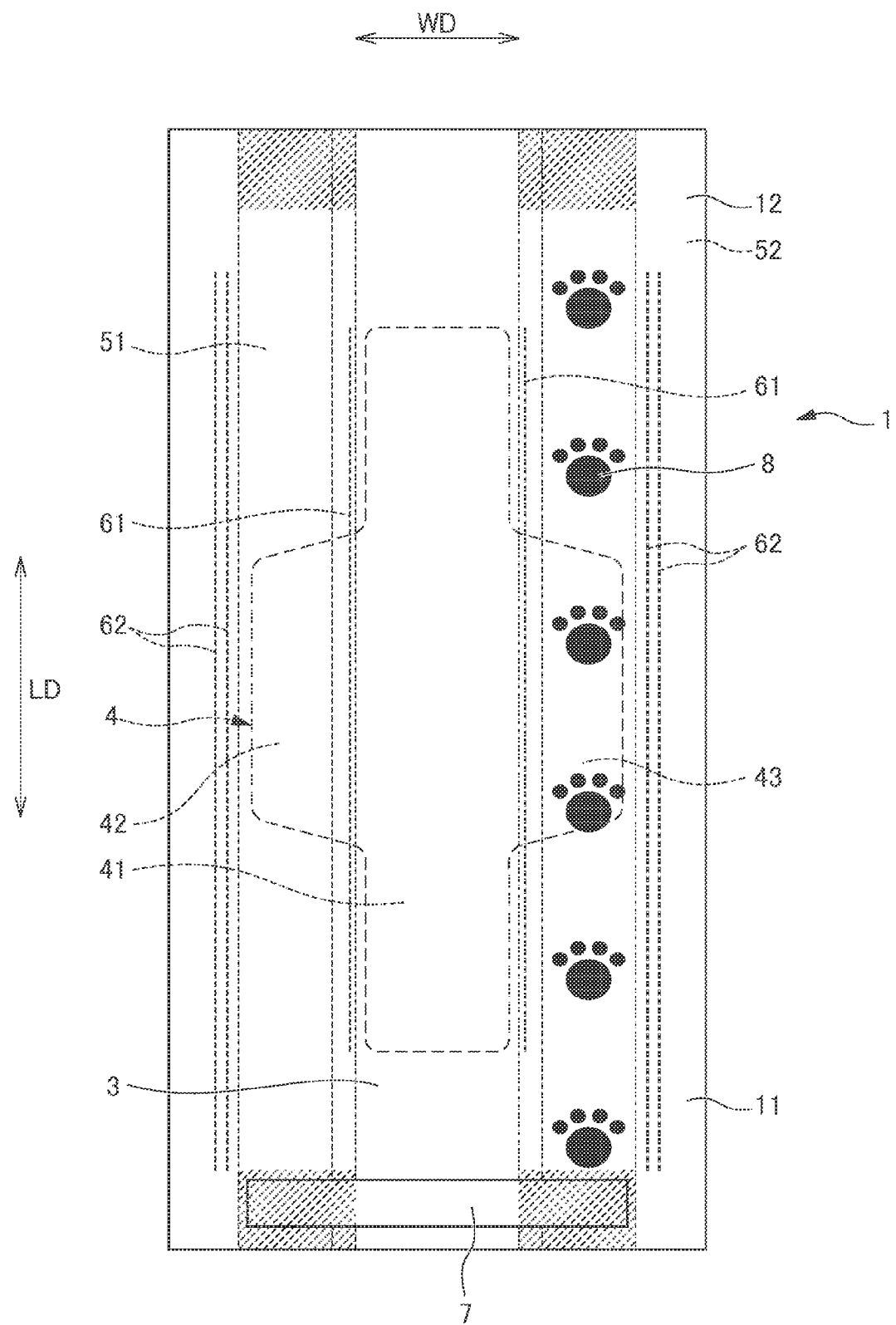
FIG. 12B is a diagram illustrating an example of arrangement of the position mark.
Figure 12C:
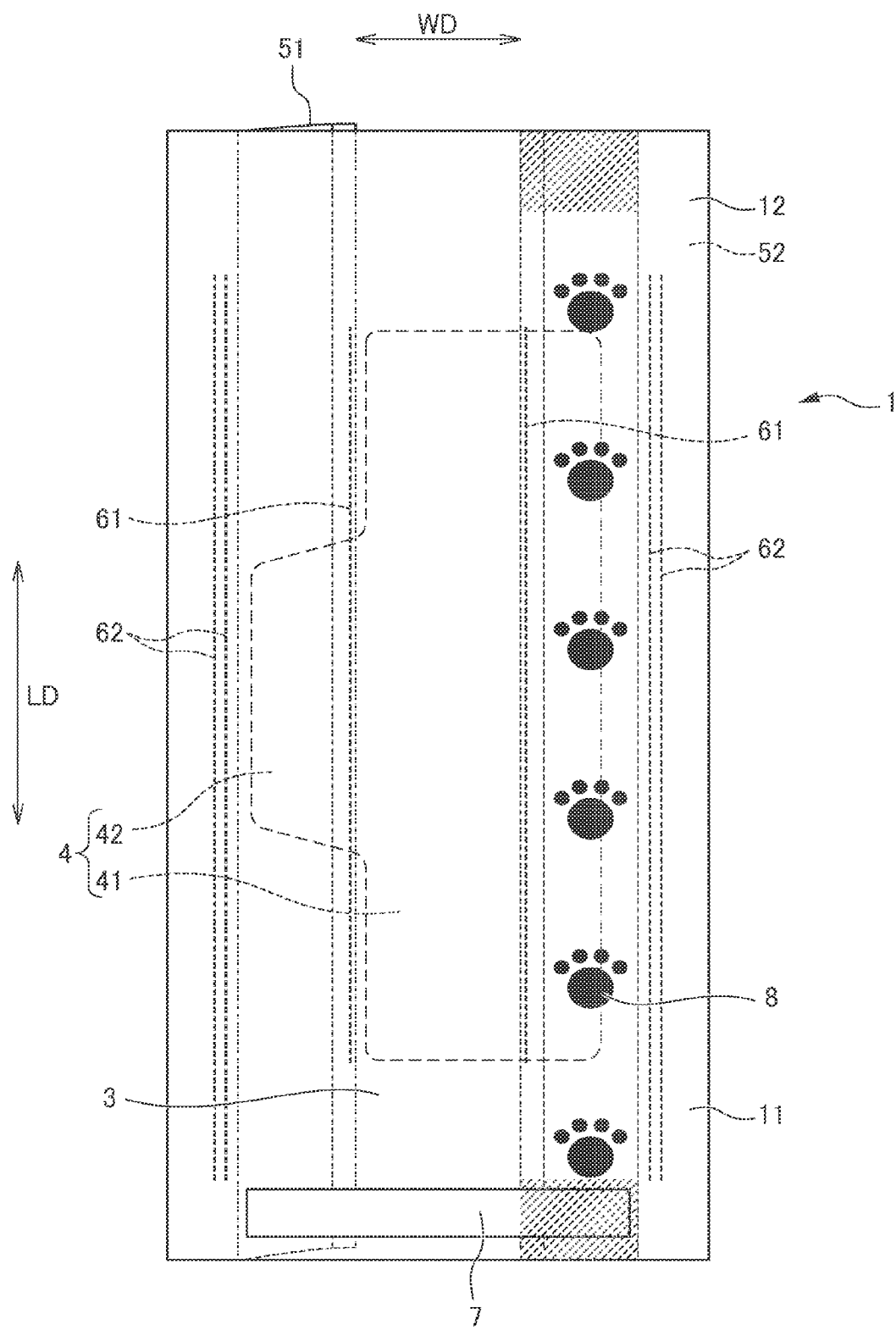
FIG. 12C is a diagram illustrating an example of arrangement of the position mark.

Yet alternatively, a plurality of position marks 8 can be disposed at predetermined intervals in the longitudinal direction LD, as shown in FIGS. 12B and 12C.

In addition, in the first embodiment, the inner edges of the first end portion and the second end portion of the second side sheet 52 in the longitudinal direction LD are joined to the top sheet 2, while the inner edges of the first side sheet 51 are not joined with the top sheet 2; however, the present invention is not limited thereto. In other words, all the inner edges of the first end portion and the second end portion in the longitudinal direction LD of the first side sheet and the second side sheet can be joined with the top sheet.

In addition, in the first embodiment, the hook tape 7 is engaged with the top sheet 2 configuring the inner face of the second end portion 12; however, the present invention is not limited thereto. In other words, a loop member with a plurality of loop portions that can engage with the hook tape can be provided on the inner face of the second end portion of the absorbent article for pet, thereby allowing the hook tape to engage with the loop member.

Furthermore, in the first embodiment and second embodiment, the back surface layer 3 is constituted of two layers: the back surface sheet 31 and the waterproof sheet 32; however, the present invention is not limited thereto. In other words, the back surface layer can also be constituted only of the back surface sheet or the waterproof sheet.

The invention claimed is:

1. An absorbent article for a pet comprising:
    a liquid permeable top surface layer;
    a liquid impermeable back surface layer;
    an absorbent core disposed between the top surface layer and the back surface layer;
    a first end portion and a second end portion of the absorbent article for the pet configured in a rectangular shape, opposite each other;
    a pair of side portions opposite each other orthogonal to the pair of the end portions, the absorbent article for pet being configured to be worn in a state of being wrapped around a waist of the pet;
    a pair of side sheets disposed on respective top surface layer sides of the pair of side portions, with outer edge joined with the top surface layer or the back surface layer;
    an elastic member attached to a vicinity of an inner edge of the pair of side sheets;
    a belt-like absorbent core main body that extends from a first end portion side to a second end portion side; and
    a first extension portion that extends outwards in a width direction from a first side edge in a central portion in a longitudinal direction of the absorbent core main body, wherein
    the pair of side sheets includes
        a first side sheet disposed on a side where the first extension portion is provided, an inner edge of the first side sheet being a free end spanning an overall length in the longitudinal direction; and
        a second side sheet disposed opposing the first side sheet, an inner edge of the second side sheet at the first end portion and the second end portion being joined to the top surface layer.

2. The absorbent article for a pet according to claim 1, further comprising:
    a pair of pocket portions formed between an inner face of the pair of side sheets and an outer face of the top surface layer,
    wherein a length of the pocket portion in the longitudinal direction of the absorbent article for the pet is greater than a length of the first extension portion in the longitudinal direction of the absorbent article for the pet.

3. The absorbent article for a pet according to claim 1, wherein
    the absorbent core further comprises a second extension portion that extends outwards in the width direction from a second side edge in the central portion in the longitudinal direction of the absorbent core main body.

4. The absorbent article for a pet according to claim 3, further comprising a position mark that indicates a position used as an index during putting on the absorbent article for pet.

5. The absorbent article for a pet according to claim 4, wherein
    the position mark is disposed at a position corresponding to: the absorbent core main body; the first extension portion; or the second extension portion.

6. The absorbent article for a pet according to claim 5, wherein
    the position mark changes in color when the absorbent core at the position where the position mark is disposed absorbs moisture.

7. The absorbent article for a pet according to claim 4, wherein
    the position mark is disposed at a position that is visually recognizable from an outer face side of the back surface layer.

* * * * *